United States Patent [19]
Reinhardt et al.

[11] Patent Number: 5,211,643
[45] Date of Patent: May 18, 1993

[54] SODIUM BICARBONATE CONTAINING PRECIPITATE-FREE DIALYSIS SOLUTIONS

[75] Inventors: Bertold Reinhardt, Oberursel; Volker Bartz, Linden, both of Fed. Rep. of Germany

[73] Assignee: Fresenius AG, Fed. Rep. of Germany

[21] Appl. No.: 528,855

[22] Filed: May 25, 1990

[30] Foreign Application Priority Data

May 26, 1989 [DE] Fed. Rep. of Germany ....... 3917251

[51] Int. Cl.$^5$ .................... A61B 19/00; A61M 5/32
[52] U.S. Cl. .................... 604/416; 604/410; 604/5; 206/221; 424/686
[58] Field of Search .............. 604/403, 410, 411, 416, 604/5; 206/219, 221, 438, 484, 524.1, 524.2, 524.6; 424/686, 687; 514/974

[56] References Cited

U.S. PATENT DOCUMENTS

| | | | |
|---|---|---|---|
| 3,978,212 | 8/1976 | Barna | 424/156 |
| 4,399,036 | 8/1983 | Babb et al. | |
| 4,507,114 | 3/1985 | Bohman et al. | 604/416 |
| 4,591,049 | 5/1986 | Walter et al. | 604/416 |
| 4,608,043 | 8/1986 | Larkin | 604/410 |
| 4,630,727 | 12/1986 | Feriani et al. | 604/416 |
| 4,663,166 | 5/1987 | Veech | 424/146 |

FOREIGN PATENT DOCUMENTS 0022922 5/1983 European Pat. Off.
0086553 4/1987 European Pat. Off.

OTHER PUBLICATIONS

Drucker, et al., Replacement of Renal Function by Dialysis, 1983; pp. 35, 148; 552.

Primary Examiner—C. Fred Rosenbaum
Assistant Examiner—Ronald K. Stright, Jr.
Attorney, Agent, or Firm—Omri M. Behr; Matthew J. McDonald

[57] ABSTRACT

Dialysis solutions for hemodialysis and the like, are prepared by addition of sufficient acid to lower the pH of a sodium carbonate solution to less than 7.6 under conditions which will retain the carbon dioxide generated by such acid addition and mixing the thus produced solution with a solution of the other ions required in such a dialysis solution, again under conditions which will retain the carbon dioxide, to provide a dialysis solution which, under working conditions, will not cause finely divided precipitates of calcium carbonate to form.

12 Claims, 1 Drawing Sheet

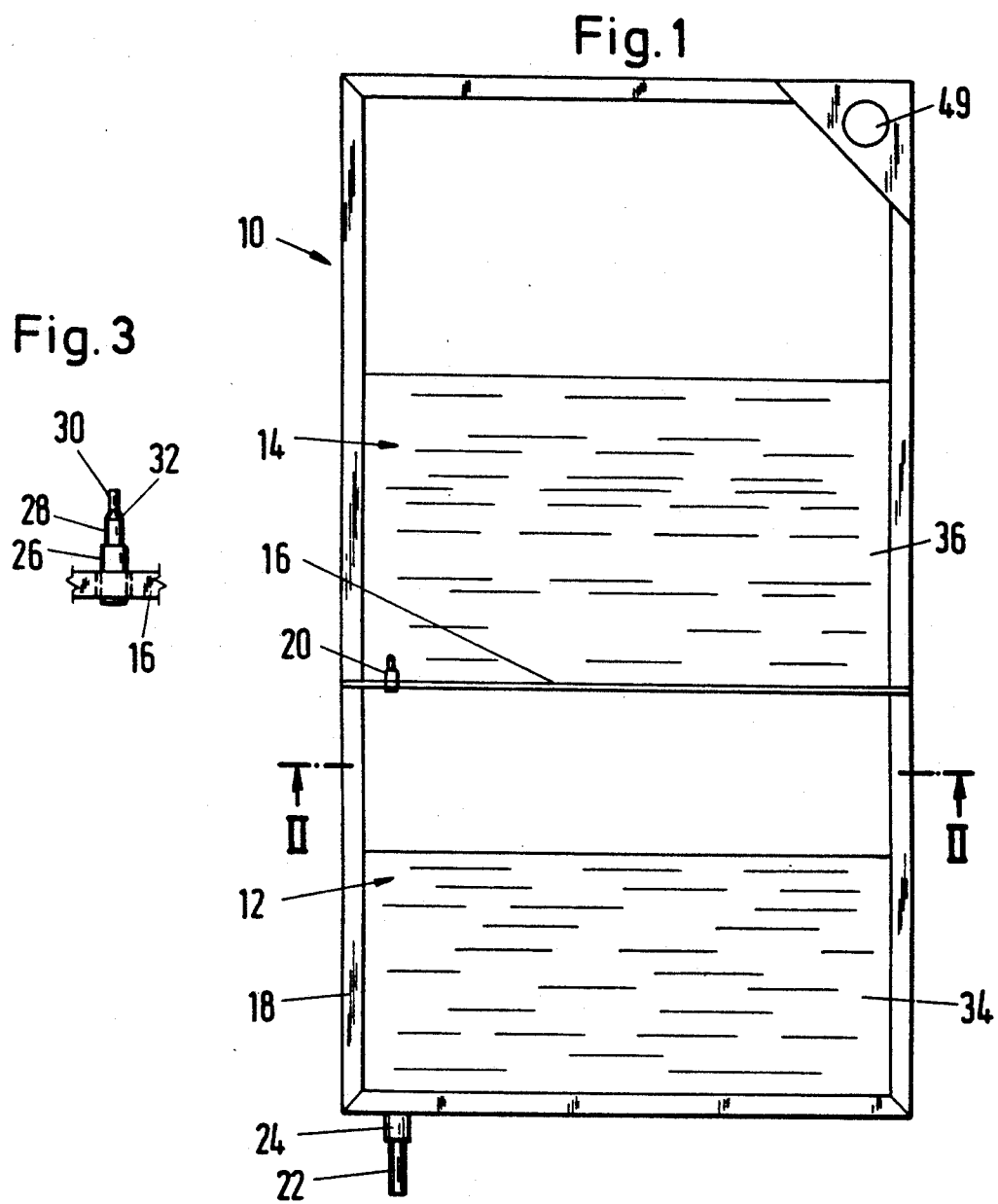

SODIUM BICARBONATE CONTAINING PRECIPITATE-FREE DIALYSIS SOLUTIONS

BACKGROUND OF THE INVENTION

1. Field of the Invention

Precipitate-free dialysis solutions.

2. Discussion of the Prior Art

The invention is concerned with a sodium bicarbonate containing concentrate for the production of a dialysis fluid for the cleaning of blood. In addition to the removal of metabolic products, one of the most important tasks of artificial kidney therapy such as hemodialysis, hemofiltration, hemodiafiltration, CAVH, CAVHD and peritoneal dialysis is the correction of metabolic acidosis. For this reason, all of the dialysis fluids used in these procedures contain a buffer. In hemodialysis, as well as in CAPD, bicarbonate in the form of sodium bicarbonate was the original buffer. However later, other buffers such as lactate (usually utilized in CAPD) or acetate usually used in hemodialysis, were utilized in place thereof.

In addition to the original technical problem of inability to control the stability of the dialysis fluids, a particular problem resided in the precipitation of calcium carbonate in these solutions constituted the reason for changing the buffer substance. In the therapy of uremic patients calcium concentrations of the order of 2 mmol/liter and bicarbonate concentrations up to 42 mmol/liter are utilized or required. Thus, because of the mode of utilization or addition of these solutions, the solubility product of calcium and carbonate is exceeded and thus, the precipitation of calcium carbonate from the solution takes place. The problem is aggravated by the precipitation of calcium carbonate in the CAPD solutions because, for reasons of sterility it is necessary to autoclave at approximately 120° C.

In hemodialysis and procedures associated therewith, bicarbonate buffer containing dialysis solutions have for several years been provided in such a way that on the one hand the basic bicarbonate concentrate, and on the other hand the calcium ion containing acidic electrolyte concentrate were maintained in separate containers (see Feriani, et al., U.S. Pat. No. 4,630,727 of Dec. 23, 1986, the disclosure of which is incorporated herein by reference). The containers are connected to the dialysis machine and only immediately before use are the two concentrates mixed together with water to form the actual dialysis fluid. Even taking these precautions in formation of the solutions, calcium carbonate precipitation still occurs in the dialysis machines which can clearly lead to disturbances in the dialysis procedure.

In order to avoid complications in the long term, the several tubing lines of the dialysis machine are regularly washed out with acids such as acetic acid and similar dilute acids, in order to remove the calcium carbonate.

The art recognizes a plurality of patents which are concerned with the production of bicarbonate containing dialysis fluids for blood cleaning. In several publications there is disclosed the utilization of an acid concentrate and a basic bicarbonate solution wherein the pH values of both concentrates are controlled by the pH of certain introduced dissociable salts, such as calcium chloride, sodium bicarbonate or sodium carbonate. Thus, additional acid can be provided to the acid concentrate in order to raise the level of acidity, that is to say, to reduce the measured pH value to provide, after mixing with a basic concentrate, the physiological pH value of 7.3.

Arrangements for the production of a bicarbonate containing dialysis fluid, concentrate, and dialysis fluids themselves are disclosed in DE-OS 3146425, EP-OS 022922 and EP-OS 086553 as well as, in patents cited in this last reference. It is common to several of these patents that no correction of the pH of the bicarbonate containing concentrate is suggested in order to reduce or even eliminate the calcium carbonate precipitation after mixing of the calcium containing concentrate. This is explicable, since the addition of the acid is known to move the bicarbonate/carbon dioxide equilibrium into the direction of carbon dioxide which means that gaseous carbon dioxide is released. This requires particular security measures for the containers since otherwise the carbon dioxide could leak out and thus cause the pH value to rise again, that is to say, the pH is pushed into the basic region.

Thus, for chemical reasons the already acidic calcium ion containing solution is further acidified with acid in order to attain the desired dialysis fluid composition upon mixing with the bicarbonate concentrate.

As in the case of hemodialysis, following the suggestion of Feriani and LaGreca, the reintroduction of bicarbonate in place of the less physiological lactate as buffer, is separated from the calcium containing electrolyte solution in a two chambered container as is described in U.S. Pat. No. 4,630,727. Further publications of these authors are to be found in Int. Art Organs (1985) pages 57 to 58, and in the Monograph Peritoneal Dialysis Proceeding of the Second International Course (1986) pages 143 to 148. With the arrangement described in these publications, in which both concentrates may be held in two mutually connectable chambers, autoclaving can be carried out without any problems. However, a calcium carbonate precipitation after the mixing or during the treatment in the peritoneal cavity cannot be avoided since, in a relatively short time after mixing (maximum two hours) calcium carbonate does precipitate, which is not a viable proposition in peritoneal dialysis.

In order to avoid the precipitation of calcium carbonate, these authors utilized dilute aqueous sodium bicarbonate that is to say, a bicarbonate content of less than 30 mmol/liter and a calcium concentration of 1.5 mols/liter in the final solution. Apart from the fact that this approach does not deal with the danger of precipitation, these bicarbonate concentrations are insufficient to adequately correct acidosis of the patient. Thus, the bicarbonate plasma level of the patients does not rise above 22 mmol/liter and usually remained below this level, while the normal bicarbonate plasma level should be of the order of 25 mmol/liter. The task of the invention therefore, is to provide a bicarbonate concentrate and a process for preparing a bicarbonate containing dialysis fluid wherein the danger is avoided that calcium carbonate precipitation occurs during the mixing step or during the time of dialysis treatment.

SUMMARY OF THE INVENTION

The sodium bicarbonate concentrate of the present invention contains as much additional acid as is physiologically acceptable to provide a pH value of the concentrate which remains below 7.6 at room temperature. This problem is achieved by introducing an acid concentrate into this concentrate. Thus, the pH value of the sodium bicarbonate solution is lowered to a level of between 7.2 and 7.4 suitably, 7.3 to 7.35 at room temperature.

The dialysis solutions produced in accordance with the present procedure are stable (i.e., will not precipitate calcium carbonate) up to a bicarbonate concentration of up to 60 mmol/liter and up to a calcium concentration of 5 mmol/liter. The required stability for the use of such a solution of CAPD is twelve hours (time overnight) is exceeded by more than double for the bicarbonate concentration necessary for the elimination of acidosis. This has been proved by initial experiments both with animals and humans.

BRIEF DESCRIPTION OF THE DRAWINGS

There is illustrated the two chamber bag of Feriani, et al., U.S. Pat. No. 4,630,727, which is the preferred mode for this invention.

FIG. 1 is a view of a bag from the side.

FIG. 2 is a section through the bag as taken on the line II—II of FIG. 1.

FIG. 3 is a view of the frangible part, placed between the two chambers of the bag, on a larger scale.

DETAILED DESCRIPTION OF THE DRAWINGS

In FIGS. 1 and 2 a container 10 will be seen that is manufactured in the form of a plastic bag. This container 10 has two chambers, a first chamber 12 and a second one 14, that are divided from each other by a dividing structure in the form of a weld seam.

Furthermore, the bag 10 has a welded marginal zone 18 by which the two chambers 12 and 14 are shut off from the atmosphere. This weld seam 18 furthermore joins with the weld seam 16 so that with the exception of the flow passage part 20, there is no flow communication between the chambers. This passage part 20 is set in the weld seam and surrounded thereby.

Furthermore, the first chamber 12 is joined to a discharge duct 22 which preferably has the weld seam 18 formed round it and is capable of producing a connection with the first chamber if the closure means 24 (that is best designed to block the discharge duct 22) is opened. This means 24 will normally be made of a plastics tube with a frangible part thereon which is broken when the package is used.

The flow passage part 20, that is to be seen on a larger scale in FIG. 3, consists of a tubular part 26, that merges with a further tubular part 28 with a smaller external diameter and which is shut off by a frangible part 30 running along the line 32 of weakness.

The first chamber 12 is advantageously filled with a bicarbonate-containing fluid 34 of pH less than 7.6, yet to be diluted, whereas the second chamber 14 is filled with solution 36 of the other ions needed in the dialysis solution. When the package is used the frangible part 30 is broken off from the flow passage part so that the acid solution 36 may make its way through the flow passage 38 into the flow passage part 20 and thence into the first chamber 12.

After the mixing of the two fluids and the production of the dialyzing fluid or the fluid to be used for hemofiltration or the infusion fluid, the closure device 24 is opened to unblock the discharge duct 22. At its other end it is provided with a conventional connection means (not illustrated) as for example a CAPD connector, a catheter, an infusion device or the like.

Lastly, the container 10 has a suspension means 49 in the form of an eye welded onto its top end.

As has been described hereinbefore, the solutions are introduced through filling slits that are not shown in the welded edge 18 into the chambers 12 and 14 that are then closed by welding. If desired, even before such welding a certain amount of gaseous carbon dioxide is run into the chamber, as for example to produce an internal pressure of 40 to 80 mm/Hg and to influence the decomposition equilibrium of the bicarbonate.

Material for plastic bags usually include laminated polymer layers. Since at least the first chamber 12 should not lose substantial amounts of $CO_2$ during storage (not more than 5% of the original value), at least one layer is preferably provided in said laminate which is substantially impermeable to gases, especially $CO_2$. For the purposes of the invention, an aluminum layer is used in said laminate.

DESCRIPTION OF THE PREFERRED EMBODIMENTS

The concentrates of the present invention that is to say, the acid concentrate A and the basic bicarbonate concentrate B can be produced in the manner generally known to those skilled in the art. It is important for the purpose of the invention that the bicarbonate solution is adjusted to a pH value of not greater than 7.6 by the addition of a physiologically tolerable acid. Acids which may be utilized include for example, hydrochloric acid or organic metabolic acids such as for example, acidic acid or lactic acid. However, it has been determined that the latter acids are less preferred since those skilled in the art wish to avoid acetate/lactate solutions. Furthermore, of course, the anhydride of carbonic acid, that is to say, carbon dioxide, may be added insofar as it will reduce the pH value of the dialysis fluid below 7.6. It must of course be taken into account that the finished concentrates should be protected by a suitable choice of containers that, carbon dioxide either in gaseous or dissolved form, cannot be permitted to dissolve out of the concentrate, which would permit the pH value to rise.

The completed dialysis solutions have the following composition ranges in mval/l.

| Ions | Operative Range (mval/l.) | Preferred Range (mval/l.) |
| --- | --- | --- |
| $Ca^{2+}$ | 0.5–5 | 1–2 |
| $Mg^{2+}$ | 0–3 | 0.5–1.55 |
| $Cl^-$ | 90.5–121 | 105–115 |
| $Na^+$ | 128–145 | 135–140 |
| $K+$ | 0–4 | 1–3 |
| $HCO_3^-$ | 25–40 | 28–35 |

A utilizable sodium bicarbonate solution which can then be mixed with a basic calcium carbonate concentrate, may suitably contain 72 mmol/liter sodium bicarbonate, wherein the pH value is reduced to a level of 7.35 to 7.4 at room temperature (25° C.) by means of the addition of hydrochloric acid.

This concentrate may be sterilized in the usual manner, by sterilization through a sterile filter (means pore size 0.2 microns), wherein the filter pressure should not exceed 1 bar by autoclaving at 120° C. In any case however, the solution should be in a sealed, substantially carbon dioxide impermeable container, otherwise carbon dioxide is lost and the equilibrium again shifts substantially to the basic side.

The basic concentrate (B) to be mixed with an acid concentrate (A) in the ratio of 1 to 1, preferably has the following composition:

196 mmol sodium chloride,
3.6 mmol calcium chloride,
1 mmol magnesium chloride.

This concentrate (B) is sterilized in a similar manner and in case of need, can be mixed with concentrate (A) under sterile conditions, for example, by means of utilizing the double chamber bag, disclosed in Feriani, et al., U.S. Pat. No. 4,630,727. On the other hand, it is also possible to employ separate vessels, i.e., bags or flasks, which comprise several chambers. These vessels are connected to each other by means of a suitable intercommunication system, i.e., a hose system. Furthermore, the solutions are suitably utilized in a ratio of from about 3:1 to about 1:3, in particular 1:1 with each other. The amounts of electrolyte, that is to say, osmotic agents, correspond to the particular degree of dilution and the desired end concentration. These vessels should have a maximum water vapor permeability of less than 1 g/m$^2$/day/bar at 20° C. as measured by DIN 53122 and a carbon dioxide permeability of less than 1 cm$^3$/100 $\mu$m/m$^2$/day/bar at 20° C. according to DIN 53380. In any case, the pH of the solution should not exceed a value difference of 0.15 between the starting and the final values.

On the other hand, such concentrates can of course be mixed in the dialysis machine for the production of dialysis fluid for hemodialysis.

The thus obtained solutions suitably contain at least 134 mmols/liter of sodium ion, 1.8 mmols of calcium ion, 0.5 mmols of magnesium ion, as well as about 34 mmols/liter of sodium hydrogen carbonate (as well as excess carbon dioxide in dissolved or ionic form, carbonate ions, as well as remaining chloride ions).

The hydrogen carbonate concentration of the ultimate dialysis fluid can be regulated in accordance with the requirements of the patient, which is a further independent preferred embodiment of the present invention. Thus, the total carbon dioxide, that is to say, tCO$_2$ of the bicarbonate content of the blood and from this the total bicarbonate content of the patient can be determined from the blood values of uraemic patient,. From this, the amount of hydrogen carbonate required to be provided to patient during treatment can be individually calculated and by an appropriate selection, a particular concentration can be utilized. Thus, by means of utilizing a concentrate in accordance with the present invention, it is possible to neutralize the patient's acidosis and the bicarbonate pool kept at a sufficient level during the dialysis treatment that no acidosis situation can again occur.

Furthermore, the introduction of a bicarbonate dialysis solution into the peritoneal cavity having a physiological pH value, has the further advantage that the natural immunities present in the peritoneal cavity are not inactivated but rather preserved.

Recent studies have in fact demonstrated that the previously conventional CAPD dialysis fluids with a pH value of 5.1 to 5.4, substantially neutralize the immunodefense mechanism of the macrophages in the peritoneal cavity, so that the danger of peritonitis by the inadvertent introduction of infected bodies exists. This can, to all intents and purposes be avoided by the utilization of a dialysis fluid having a physiological pH.

As has already been shown, dialysis fluids of different bicarbonate contents, can be formulated from correspondingly provided concentrates, wherein the bicarbonate content is at least 20 mmol/liter. Preferably, the bicarbonate content in the completed solution should lie between 25 and 40 mmol/liter. It will therefore be understood that the actual amount of bicarbonate charged must be rather higher since bicarbonate is in equilibrium with carbon dioxide and when the pH value drops from original 8 to 8.8 to 7 to 7.4, carbon dioxide is formed from hydrogen carbonate. The amount of this carbon dioxide of course depends on the pH value and generally speaking, corresponds to 5 to 10% of the original hydrogen carbonate value so that the initially provided hydrocarbonate amount must be correspondingly corrected.

The additional acid causes the release of 2 to 5 mmol/liter of carbon dioxide from the hydrogen carbonate which is physically dissolved in the mixture and is equilibrium with the CO$_2$, provided however that the CO$_2$ cannot escape from the system after acid addition is complete. Thus, the final solution can have a partial pressure of pCO$_2$ of the order of 50 to 90 mm/Hg.

In place of the two solutions (A) and (B), it is possible to utilize three solutions, namely, an acid solution (A), a sodium bicarbonate solution (B1) and a further acid solution (B2). Thus, solutions (B1) and (B2) can be first mixed in such a manner that (B2) has such a level of acidity that the final solution has a pH value of no more than 7.6, as has been stated hereinabove. This hydrocarbonate solution then corresponds to the above described concentrate (B) which can then be mixed with concentrate (A).

The final dialysis fluid should have a physiological electrolyte content which can vary from case to case to be patient specific. Thus, within this physiological area, there are certain formulation possibilities. For the circumstance that the bicarbonate containing solution should have osmotic properties, which is necessary for utilization in CAPD, there is added an osmotic reactive agent in the appropriate amount. For this, glucose is particularly suitable. In the present case, the acid component comprises 20 to 90 grams of glucose/liter which, under a 1:1 dilution yields an osmolarity of the solution of 350 to 550 mosm/liter. It is advantageous to hold the pH value of the acid concentrate which also contains the glucose, to a level of no less than 5.5 to 6.2. This ensures that during the sterilization at elevated temperatures, i.e., 121° C., the caramelization of the glucose is avoided. This rather low level of acidity of the acid solution hardly alters the pH value of the mixture with respect to the pH value of the basic concentrate (B), since the buffer capacity of the sodium bicarbonate buffer readily buffers such a small number of protons.

In both concentrates (A) and (B), only such ions are held apart which, when combined, cause the precipitation of low solubility carbonate, otherwise the only practical considerations need be taken into account, in which the concentration of the remaining components is considered. Thus, solution (B) contains calcium and magnesium salts and concentrate (A) sodium hydrogen carbonate, otherwise other criteria, for example, the level of acidity for the caramelization of glucose determine in which concentrates the remaining components, i.e., potassium chloride, sodium chloride and the like, are placed.

The following example illustrates the invention:

EXAMPLE I

Concentrate A 76 mmol sodium hydrogen carbonate were weighed into one liter of water. Subsequently, the thus obtained solution was treated with 1 mmol. hydrochloric acid to attain a pH value of 7.35 to 7.4. The entire solution was filtered to be pyrogen free.

In place of hydrochloric acid, acetic or lactic acid may be used or, if desired, $CO_2$ may be bubbled in at atmospheric or slightly elevated pressures (up to 2 bar) to achieve the desired pH value.

Concentrate B
196 mmol of sodium chloride.
3.0 mmol of calcium chloride dihydrate,
1 mmol magnesium chloride hexahydrate,
1.66 mmol glucose monohydrate,
are weighed out, mixed with water and made up to 1 liter. The pH value is adjusted to 5.5 with a few drops of N-normal hydrochloric acid.

Both concentrates, before heat sterilization, are filled into a 2-chamber container (as in U.S. Pat. No. 4,630,727), whose chambers are connectable to each other by a breakable connecting arrangement to bring the fluids into mutual contact.

The concentrate (B) is placed in that chamber which is in connection with an outflow opening.

EXAMPLE II

Use of Concentrates

The bag containing the two concentrates is sterilized at about 121° C. The sterilization takes place preferably in an autoclave containing sufficient water and carbon dioxide to counter the partial pressure thereof in the bag. In order to mix both concentrates, the frangible connector is broken, whereby the concentrate (A) is forced by the gas over pressure of the bag into the bicarbonate concentrate (B). The mixing of the concentrates is achieved by transferring the solutions back and forth between the chambers of the container.

This yields a bicarbonate solution for CAPD, having the following concentration:

| Sodium | 136 mmol/l |
| Calcium | 1.5 mmol/l |
| Magnesium | 0.5 mmol/l |
| Glucose | 0.84 mmol/l |
| Hydrogen carbonate | ca. 37 mmol/l |
| Chloride | ca. 103 mmol/l |
| pH | 7.3 |

This solution does not show any precipitation of calcium carbonate over an observation period of 6 hours and can be utilized for CAPD in the usual manner.

I claim:

1. A delivery system for the delivery of sodium bicarbonate containing fluids for dialysis and the like, comprising:
   a) a container having at least one means of egress for liquid, containing an aqueous solution comprising at least sodium bicarbonate of between 25 and 40 meq/l. of bicarbonate ion at pH below 7.6; said container having a water vapor permeability of less than 1 g/m²/day/bar as measured by DIN 53122 and a carbon dioxide permeability of less than 1 cm³/100 μm/m²/day/bar at 20° C. as measured by DIN 53380;
   b) a container having at least one means of ingress for liquid and at least one means of egress for liquid containing an aqueous solution comprising between 0.1 and 10 meq./l. of $Ca^{2+}$, 0 to 6 meg./l. $Mg^{2+}$, 90.5 to 121 meq./l. $Cl^-$, 180–290 meq./l. $Na^+$;

wherein the egress means of (a) is connected to the ingress means of (b).

2. A delivery system in accordance with claim 1, wherein the amount of sodium bicarbonate content is sufficient to bring the hydrogen carbonate content of the mixed fluid in both chambers to at least 20 mmol.

3. A delivery system in accordance with claim 2, wherein the hydrogen carbonate content of the mixed fluid in both chambers contains 25 to 40 mmol of bicarbonate.

4. A delivery system in accordance with claim 3, wherein the sodium bicarbonate solution has a pH of 7.2 to 7.4.

5. A delivery system of claim 1, wherein the container is:
   a) an outer bag structure of organic polymer having at least two chambers,
   b) a first of said chambers filled with said bicarbonate containing solution,
   c) a second of said chambers filled with said solution of other ions,
   d) an openable flow blocking valve connecting said first with said second chamber, said valve being the sole ingress or egress means to said second chamber, and
   e) at least one discharge tube fitted with a removable closure, said discharge tube passing through and being sealed to said outer bag and into a said first chamber.

6. A delivery system of claim 1, wherein the pH value is adjusted by a physiologically acceptable acid.

7. A delivery system of claim 6, wherein the acid is hydrochloric acid.

8. A delivery system of claim 6, wherein the acid is carbonic acid.

9. A method of producing a dialysis solution which comprises:
   a) adding a physiologically acceptable acid to an aqueous solution of sodium bicarbonate having an original pH exceeding 8 to reduce the pH thereof to less than 7.6;
   b) sterilizing the said solution under conditions which will retain the carbon dioxide generated by said acid addition therein;
   c) preparing a basic solution containing all of the other ions required to form said dialysis solution;
   d) sterilizing said basic solution;
   e) mixing said bicarbonate solution and said basic solution under conditions which will retain the carbon dioxide generated by the acid added to said bicarbonate solution.

10. Sodium bicarbonate-containing aqueous concentrate, which is substantially free from calcium ion, for mixing with a second calcium ion-containing concentrate, which is substantially free of bicarbonate ion, for the production of a dialysis fluid suitable for hemo or peritoneal dialysis containing the following composition in mval per liter:

$Ca^{2+} = 0.5–5$
$Mg^{2+} = 0–3$
$Cl^- = 90.5–121$
$Na^+ = 128–145$
$K^+ = 0–4$
$HCO_3 = 25–40$ characterized thereby that the sodium bicarbonate-containing aqueous concentrate, prior to mixing with said calcium ion-containing concentrate, has added thereto a sufficient amount of physiologically acceptable acid to bring the pH value of said bicarbonate-containing aqueous concentrate below 7.6 and is held in a container which is substantially impermeable to water vapor and carbon dioxide.

11. Sodium bicarbonate-containing aqueous concentrate in accordance with claim 10 characterized thereby that the pH value lies in the physiological range of 7.2 to 7.4.

12. Sodium bicarbonate-containing aqueous concentrate in accordance with claim 10 characterized thereby that the pH value is adjusted by hydrochloric acid.

* * * * *